(12) United States Patent
Zinnen et al.

(10) Patent No.: US 11,324,767 B2
(45) Date of Patent: May 10, 2022

(54) DRUG COMBINATION TREATMENTS USING BONE-TARGETING THERAPEUTICS FOR BONE AND BONE-RELATED DISEASE

(71) Applicant: MBC Pharma, Inc., Aurora, CO (US)

(72) Inventors: Shawn Zinnen, Aurora, CO (US); Alexander Karpeisky, Aurora, CO (US)

(73) Assignee: MBC PHARMA, INC., Aurora, CO (US)

( * ) Notice: Subject to any disclaimer, the term of this patent is extended or adjusted under 35 U.S.C. 154(b) by 153 days.

(21) Appl. No.: 16/476,043

(22) PCT Filed: Jan. 5, 2018

(86) PCT No.: PCT/US2018/012693
§ 371 (c)(1),
(2) Date: Jul. 3, 2019

(87) PCT Pub. No.: WO2018/129399
PCT Pub. Date: Jul. 12, 2018

(65) Prior Publication Data
US 2019/0350958 A1    Nov. 21, 2019

Related U.S. Application Data

(60) Provisional application No. 62/442,806, filed on Jan. 5, 2017.

(51) Int. Cl.
| | | |
|---|---|---|
| A61K 31/7068 | (2006.01) | |
| A61P 19/08 | (2006.01) | |
| A61P 35/04 | (2006.01) | |
| A61K 31/337 | (2006.01) | |
| A61K 51/04 | (2006.01) | |

(52) U.S. Cl.
CPC ........ A61K 31/7068 (2013.01); A61K 31/337 (2013.01); A61K 51/0491 (2013.01); A61P 19/08 (2018.01); A61P 35/04 (2018.01)

(58) Field of Classification Search
CPC .............. A61K 31/7068; A61K 31/337; A61K 51/0491; A61P 19/08; A61P 35/04
See application file for complete search history.

(56) References Cited

U.S. PATENT DOCUMENTS

| | | |
|---|---|---|
| 6,214,812 B1 | 4/2001 | Karpeisky et al. |
| 6,750,340 B2 | 6/2004 | Padioukova et al. |
| 6,896,871 B2 | 5/2005 | Karpeisky et al. |
| 7,598,246 B2 | 10/2009 | Dixon et al. |
| 8,586,781 B2 | 11/2013 | Karpeisky et al. |
| 2009/0227544 A1 | 9/2009 | Karpeisky et al. |
| 2009/0311237 A1 | 12/2009 | Frost |

FOREIGN PATENT DOCUMENTS

WO    WO 2015082322    6/2015

OTHER PUBLICATIONS

Cole et al., Targeted delivery to bone and mineral deposits using bisphosphonate ligands, Advanced Drug Delivery Reviews 99 ( 2016) 12-27, Available online Oct. 19, 2015. (Year: 2015).*
O'Day et al., Novel therapeutic agents for osteosarcoma, Expert Rev. Anticancer Ther. 9(4), 511-523 (2009) . (Year: 2009).*
Cole et al., Targeted delivery to bone and mineral deposits using bisphosphonate ligands, Advanced Drug Delivery Reviews 99 ( 2016) 12-27. (Year: 2016).*
Navid et al., Combination of Gemcitabine and Docetaxel in the Treatment of Children and Young Adults With Refractory Bone Sarcoma, Published online May 16, 2008 in Wiley InterScience. (Year: 2008).*
Chou, Theoretical Basis, Experimental Design, and Computerized Simulation of Synergism and Antagonism in Drug Combination Studies, Pharmacol Rev 58:621-681, 2006. (Year: 2006).*
El-Mabhouh, Evaluation of novel bisphosphonate conjugates for targeted therapy for bone metastases in advanced breast cancer, Edmonton, Alberta Spring 2009. (Year: 2009).*
Leu et al. (2004) "Laboratory and Clinical Evidence of Synergistic Cytotoxicity of Sequential Treatment with Gemcitabine Followed by Docetaxel in the Treatment of Sarcoma" Journal of Clinical Oncology 22(9):1706-1712.
Bayer Healthcare Pharmaceuticals Inc. (2013) "Highlights of Prescribing Information, Xofigo Injection" https://www.accessdata.fda.gov/drugsatfda_docs/label/2013/20397ibl.pdf.
Berlin et al. (1993) "Development of a novel spontaneous metastasis model of human osteosarcoma transplanted orthotopically into bone of athymic mice" Cancer Research 53:4890-4895.
Bulinski (1997) "Overexpression of MAP4 inhibits organelle motility and trafficking in vivo" J Cell Sci. 110:3055-3064.
Chou et al. (1984) "Quantitative analysis of dose-effect relationships: the combined effects of multiple drugs or enzyme inhibitors" Adv. Enzyme Reg. 22:27-55.
Cole et al. (2016) "Targeted Delivery to Bone and Mineral Deposits Using Bisphosphonate Ligands" Advanced Drug Deliver Reviews 99:12-27.

(Continued)

*Primary Examiner* — Robert A Wax
*Assistant Examiner* — Randeep Singh
(74) *Attorney, Agent, or Firm* — FisherBroyles, LLP; Cara L. Crowley-Weber (57) ABSTRACT

Provided herein is a novel method for creating fixed, non-antagonistic molar ratios of drugs in and around the bone environment for desired periods of time. This method enables treating bone and bone-related disease by administering a pharmaceutical composition comprising a bone-targeted therapeutic agent able to release a drug payload from the bone surface, in addition to a second therapeutic agent. Such methods are useful in the treatment of bone and bone-related diseases, such as cancer-induced bone disease, osteomyelitis and bone infection, bone pain and inflammatory bone disease, metabolic disease, as well as others.

12 Claims, 7 Drawing Sheets

(56) References Cited

OTHER PUBLICATIONS

Gralow et al. (2007) "Managing Metastatic Bone Pain: The Role of Bisphosphonates" Journal of Pain and Symptom Management 33(4):462-472.
International Search Report from PCT/US18/12693 dated Mar. 12, 2018.
Lilly USA, LLC (2014) "Highlights of Prescribing Information, Gemcitabine for Injection" https://www.accessdata.fda.gov/drugsatfda_docs/label/2013/20397ibl.pdf.
Mayer et al. (2006) "Ratiometric dosing of anticancer drug combinations: controlling drug ratios after systemic administration regulates therapeutic activity in tumor-bearing mice" Mol. Cancer Ther. 5:1854-1863.
Muhlradt (1997) "Epothilone B stabilizes microtubuli of macrophages like taxol without showing taxol-like endotoxin activity" Cancer Res. 57:3344-3346.
Nicolaou (1997) "Synthesis of epothilones A and B in solid and solution phase" Nature 387:268-272.
Palmerini et al. (2016) "Gemcitabine and Docetaxes in Relapsed and Unresectable High-Grade Osteosarcoma and Spindle Cell Sarcoma of Bone" BMC Cancer 16:1-8.
Panda (1996) "Differential effects of vinblastine on polymerization and dynamics at opposite microtubule ends" J. Biol. Chem. 271:29807-29812.
Panda (1997) "Stabilization of microtubule dynamics by estramustine by binding to a novel site in tubulin: a possible mechanistic basis for its antitumor action" Proc Natl. Acad. Sci USA 94:10560-10564.
Reingolz et al. (2010) "A Promising Approach for Treatment of Tumor-Induced Bone Diseases: Utilized Bisphosphonate Derivates of Nuceloside Antimetabolites" 47(1):12-22.
Sandoz Inc. (2012) "Highlights of Prescribing Information, Docetaxel Injection" https://www.accessdata.fda.gov/drugsatfda_docs/label/2012/201525s002ibl.pdf.
Vasquez (1997) "Nanomolar concentrations of nocodazole alter microtubule dynamic instability in vivo and in vitro." Mol. Biol. Cell 8:973-985.
Magnetto et al. (1999) "Additive antitumor activities of taxoids in combination with the bisphosphonate ibandronate against invasion and adhesion of human breast carcinoma cells to bone" Int. J. Cancer 83:263-269.
Zinnen (2015) "Novel Bone-Targeting Combination Therapy for Osteosarcoma" https://grantome.com/grant/NIH/R43-CA203166-01.
El-Mabhouh et al. (2011) "A conjugate of gemcitabine with bisphosphonate (Gem/BP) Shows Potential as a targeted bone-specific therapeutic agent in an animal model of human breast cancer bone metastases" Oncology Research 19:287-295.

* cited by examiner

Chemical structures of MBC-11 and GEM-IB

Figure 2

GEM-IB in combination with DTX shows the higher efficacy. Tumor volume estimated as an ellipsoid. Volume was subtracted from day zero volume to estimate a "normal" leg volume. After day 8, ANOVA reveals a statistical significance between the mock and GEM-IB+DTX groups. 8 mice in each treatment group were averaged. Error bars represent SEM.

Figure 3

GEM-IB in combination with DTX increases time before euthanasia. Mice were euthanized when largest tumor-laden leg diameter reached 10mm above normal leg diameter. Mice in Mock and GEM+IB were sacrificed starting day 24 after treatment initiation, GEM-IB starting day 28, GEM+DTX and GEM-IB+DTX starting day 30. Mice euthanized for weight loss are not indicated as deaths in this chart, and are indicated as tick marks on day euthanized. ANOVA indicates statistical significance with p=0.0012, and multiple comparisons shows significance between the GEM-IB + DTX group with mock and GEM+DTX groups

DRUG COMBINATION TREATMENTS USING BONE-TARGETING THERAPEUTICS FOR BONE AND BONE-RELATED DISEASE

CROSS-REFERENCE TO RELATED APPLICATIONS

This application is a National Stage Application of PCT/US2018/012693, filed Jan. 5, 2018, which claims the benefit under 35 USC § 119(e) of U.S. Provisional Application No. 62/442,806, filed Jan. 5, 2017, each of which are incorporated herein by reference. To the extent appropriate, a claim of priority is made to each of the above-disclosed applications.

TECHNICAL FIELD

Compositions and methods are provided for creating fixed, non-antagonistic molar ratios of drugs in and around the bone environment for desired periods of time, that may relate to the fields of medicine, pharmacology and biochemistry. The present invention relates to the use of bone-targeted therapeutics—that create a concentration gradient of drug from highest at the bone mineral surface to lowest in the vasculature—used in combination with other drugs to enable non-antagonistic molar ratios of drugs within the bone microenvironment. This will provide a means of treating the bone and surrounding bone environment with combinations of drugs at ratios known to be efficacious in soft tissues but prior to the current invention would be unable to achieve those required ratios for sufficient time within the bone environment.

BACKGROUND

Drug combinations have been a common therapy for many diseases, including cancers and infectious diseases. The amounts of each drug in a dose combination are typically determined empirically, and are most often arrived at by using the maximum tolerated dose of a drug and then increasing a second drug dose until limited by toxicity; while both drug amounts may be adjusted, the outcome is primarily based on tolerability. This approach may not find the optimal molar drug ratios nor achieve the duration for which those ratios must be maintained in the target tissues of patients and promotes excessive toxicity. The current invention provides a novel approach to achieving molar ratios of drugs and maintaining those ratios in and around the bone for extended periods of times that are not otherwise possible.

The present invention is directed toward overcoming one or more of the problems discussed above.

BRIEF DESCRIPTION OF THE DRAWINGS

FIG. 1. The graph's background is a scale representation of the bone microenvironment. Bone mineral is lined by a row of osteoblasts (10 microns/side), followed by marrow cells of approximately the same size proceeding outward from the bone mineral: metastatic cancer cells are represented in green and modeled at the mean distance (~40 microns) they are reportedly found from bone mineral, and blood vessel's median distance from bone mineral is 90 microns and represented in red with internal erythrocytes to scale. The four graphs illustrate the consequent drug gradients in four dosing scenarios: Top-Left—Intravenous (IV) cytarabine (araC) is dosed to achieve 5-10 uM concentration in the blood for efficacious treatment of hematologic cancers; a first-order-exponential gradient from blood vessel to the bone is modeled—blue curve—and demonstrates the intervening cells are not exposed to efficacious concentrations of araC—this includes the inability to adequately dose cancer cells close to the bone mineral and helps explain the observation of cancer drug's inability to halt the growth of bone metastases. Top-Right—The gradient of araC achieved after administration of bone-targeted conjugate of araC has enabled accumulation of the conjugate on the bone mineral the release of araC and the resulting concentration gradient is modeled—blue curve. In this scenario bone-localized cancer cells are exposed to an active amount of araC. Bottom-Left—The gradient of araC—blue curve—and the gradient of a second IV drug—red curve—are shown and their molar ratios possible between the bone mineral and blood vessel are shown; in the case where non-antagonistic molar ratios greater 1:2 (0.5) are needed no efficacy can be achieved. Bottom-Right—The gradient of araC—blue curve—after release from bone-targeted drug conjugate and the gradient of a second IV drug—red curve—are shown and their molar ratios possible between the bone mineral and blood vessel are shown; in the case where non-antagonistic molar ratios greater 1:2 (0.5) are needed it can be seen efficacious ratios can be achieved 1:1-4:1 (1-4-fold).

FIG. 2. Examples of bone-targeting drug conjugates are provided. MBC-11 was tested in recently completed phase I clinical trials in patients with CIBD. Encouraging preclinical results in models of multiple myeloma, as well as prostate and breast cancer-induced bone disease, led to the initial clinical trials inclusion of patients with any primary cancer that has induced a bone lesion. Across a total of 15 patients, 206 bone lesions were imaged (18F-FDG-PET/CT), and 111 lesions were observed to have a significant reduction (>25%) in glucose avidity; thus 53.8% of bone lesions were significantly reduced in activity after MBC-11 therapy. This provides Human proof-of-concept for MBC-11 and rivals the efficacy reported for breast cancer patients receiving Xofigo. GEM-IB, MBC Pharma's 2nd generation bone-targeted conjugate, was tested in vivo in a model of prostate cancer induced bone disease. While the study was not designed for a survival endpoint, an improved survival trend was observed. Moreover, metastases were significantly reduced after treatment. In this study GEM-IB is surprisingly more active as compared to GEM-etidronate (GEM-ET), MBC-11 and cytarabine-IB. Dosing of GEM-IB at 6 mg/kg/day for five sequential days is the MTD for this dosing regimen; in addition, Monday, Wednesday and Friday dosing for three weeks at twice that daily dose was well tolerated. Accumulation on the bone can drive toxicity above the MTD. Providing enough time for GEM to be released from the bone prior to the next dose reduces toxicity. The example below provides pre-clinical proof-of-concept for GEM-IB.

FIG. 4 illustrates the benefit of GEM-IB in combination with docetaxel with regard to tumor reduction and survival benefit in a murine model of osteosarcoma. GEM-IB in combination with DTX increases time before euthanasia. Mice were euthanized when largest tumor-laden leg diameter reached 10 mm above normal leg diameter. Mice in Mock and GEM+IB were sacrificed starting day 24 after treatment initiation, GEM-IB starting day 28, GEM+DTX and GEM-IB+DTX starting day 30. Mice euthanized for weight loss are not indicated as deaths in this chart, and are indicated as tick marks on day euthanized. ANOVA indicates statistical significance with p=0.0012, and multiple comparisons shows significance between the GEM-IB+DTX group with mock and GEM+DTX groups FIG. 5 predicts cancer cell activity after combination treatment with gemcitabine-ibandronate conjugate and Xofigo.

SUMMARY OF THE INVENTION

In one aspect, provided herein is a method to treat bone or bone-related disease in a subject, said method comprising administering to said subject a pharmaceutical composition comprising a non-antagonistic molar ratio of a bone-targeted drug and a second drug. The said method is dependent upon the ability of the bone-targeted drug—in the presence of the second drug—to establish and maintain the non-antagonistic ratio in the bone compartment for a time sufficient to provide efficacy. The disclosed methods also facilitate the administration of drugs at significantly lower dose intensity while maintaining therapeutic benefit and simultaneously reducing toxicity.

FIG. 1 illustrates the comparison of dosing of the bone microenvironment by (i) the standard method—both drugs being systemically administered (right side) and (ii) the current invention—one drug release from its bone depot while the second is systemically administered (left side). While the gradients shown represent the spatial distribution of drug concentrations at a single time point, it must be understood that the ability to maintain effective ratios (at the bone compartment) over time sufficient to observe benefit can be adjusted and optimally established. The amount of bone-targeted drug administered can be adjusted to increase or decrease the drug in depot on the bone. The kinetics of drug release from the bone can be adjusted based upon the conjugation chemistry used in the bone-targeted agent. And the second systemically administered agent can be administered as an infusion for a time allowing the establishment of steady state levels in the bone environment. Regarding the ability of conjugation chemistry to affect the kinetics of drug release from the bone-targeting drug, it is understood that the chemical stability of the bond joining a drug to a bone-targeting agent (see FIG. 2 for an example) can dictate the rate of hydrolysis and drug release: for example, hydrolysis of a phosphodiester linkage would be orders of magnitude more rapid than a phosphonate linkage. In addition to chemical stability of the bond, the steric bulk of the drug and the bone-targeting agent can affect both chemical and/or enzymatic hydrolysis rates effecting drug release kinetics.

FIG. 1 illustrates the core invention is a method of creating drug ratios in the space between the bone and the vasculature. The exemplary ratios shown in the bottom panels make it clear that these ratios could not be achieved if both drugs diffused from the blood to the bone. The control of the amount and rate of release of a drug from the bone surface in combination with the control of the amount and rate of drug entering from the vasculature enables the establishment of drug ratios known to be efficacious in the bone compartment.

In one aspect, provided herein is a method (creating fixed, non-antagonistic molar ratios of drugs in and around the bone environment for desired periods of time) that uses known, or published non-antagonistic drug ratios determined experimentally in vitro, or in vivo or clinically—but not known to be effective in and around the bone—to be reproduced at the known drug ratios in the bone compartment by the current invention. For example, cytarabine in combination with daunorubicin has been used to treat acute myeloid leukemia for more than four decades and remains the backbone of therapy for this disease. Treatment protocols are designed to achieve a circulating concentration of both therapeutics in the micromolar range. However, neither therapeutic targets the bone, and as such, the combination is ineffective in treating bone cancer as the necessary concentration cannot be achieved without toxicity to the patient.

Disclosed herein are methods of using bone targeting conjugates in combination with a second therapeutic in doses that provide the desired drug ratios at the bone compartment. By conjugating cytarabine to a bisphonphonate carrier, for example, the cytarabine is delivered to the bone compartment achieving a therapeutically relevant dose at the diseased tissue. The dose of daunorubicin can be adjusted to achieve the desired concentration in the drug compartment. Various dosing regimen for a plethora of therapeutics have been clinically tested and provide a range of drug ratios as standard treatment protocols that, when used with bone-targeting technology, can be translated to achieving the therapeutically relevant dose at the bone compartment. To those skilled in the art, the wide range of combination chemotherapies currently used clinically can be translated to treat bone diseases with the use of the current invention.

In one aspect, provided herein is a method that uses non-antagonistic drug ratios that can readily be determined by those skilled in the art using the Chou-Talalay method for drug combination determination in an in vitro setting.

In one aspect, provided herein is a method that treats said subject with cancer-induced bone disease with a non-antagonistic ratio of bone-targeted cytarabine and radium (223) chloride (Xofigo™) The amount of bone-targeted cytarabine administered will be within 0.1-1-fold the maximum tolerated dose (MTD) and the amount of radium (223) chloride administered will be within 0.1-1-fold its clinically prescribed standard dose. In one embodiment the Xofigo will be administered up to 48 hours prior to administration of bone-targeted cytarabine. In another embodiment both agents will be co-administered. In another embodiment, the radium will be administered up to 48 hours after administration of bone-targeted cytarabine is complete.

In one embodiment the method treats said subject with cancer-induced bone disease with a non-antagonistic ratio of bone-targeted gemcitabine and radium (223) chloride (Xofigo). The amount of bone-targeted gemcitabine administered will be within 0.1-1-fold the maximum tolerated dose (MTD) and the amount of radium (223) chloride administered will be within 0.1-1-fold its clinically prescribed standard dose. In one embodiment the radium will be administered up to 48 hours prior to administration of bone-targeted gemcitabine. In another embodiment both agents will be co-administered. In another embodiment, Xofigo will be administered up to 48 hours after administration of bone-targeted gemcitabine is complete.

In one embodiment the method treats said subject with cancer-induced bone disease with a non-antagonistic ratio of bone-targeted gemcitabine and docetaxel. The amount of bone-targeted gemcitabine administered will be within 0.1-

1-fold the MTD and the amount of docetaxel administered will be within 0.1-1-fold its clinically prescribed standard dose. In one embodiment the docetaxel will be administered up to 48 hours prior to administration of bone-targeted gemcitabine. In another embodiment both agents will be co-administered. In another embodiment, the docetaxel will be administered up to 48 hours after administration of bone-targeted gemcitabine is complete.

In one embodiment the method treats said subject with cancer-induced bone disease with a non-antagonistic ratio of bone-targeted cytarabine and docetaxel. The amount of bone-targeted cytarabine administered will be within 0.1-1-fold the maximum tolerated dose (MTD) and the amount of docetaxel administered will be within 0.1-1-fold its clinically prescribed standard dose. In one embodiment the docetaxel will be administered up to 48 hours prior to administration of bone-targeted cytarabine. In another embodiment both agents will be co-administered. In another embodiment, the docetaxel will be administered up to 48 hours after administration of bone-targeted cytarabine is complete.

In one aspect, provided herein is a method that treats said subject with osteomyelitis with a non-antagonistic ratio of bone-targeted antibiotic and a second free antibiotic.

In one aspect, provided herein is a method that treats said subject with a viral infection with a viral load in the bone marrow compartment with a non-antagonistic ratio of bone-targeted antiviral agent and a second free anti-viral agent.

In one aspect, provided herein is a method that treats said subject with bone pain with a non-antagonistic ratio of bone-targeted analgesic or anesthetic and a second free analgesic or anesthetic.

In one aspect, provided herein is a method that treats said subject with rheumatoid arthritis or an inflammatory bone condition with a non-antagonistic ratio of bone-targeted anti-inflammatory and a second free anti-inflammatory.

In one aspect, provided herein the composition comprises the bone targeted conjugates claimed in patent numbers: U.S. Pat. Nos. 6,214,812 and 6,750,340 and 6,896,871 and 7,598,246 in combination with any of the following drugs from:

Classes of compounds that may be used as cytotoxic agents include the following: alkylating agents (including, without limitation, nitrogen mustards, ethylenimine derivatives, alkyl sulfonates, nitrosoureas and triazenes): uracil mustard, chlormethine, cyclophosphamide (Cytoxan®), ifosfamide, melphalan, chlorambucil, pipobroman, triethylene-melamine, triethylenethiophosphoramine, busulfan, carmustine, lomustine, streptozocin, dacarbazine, and temozolomide; antimetabolites (including, without limitation, folic acid antagonists, pyrimidine analogs, purine analogs and adenosine deaminase inhibitors): methotrexate, 5-fluorouracil, floxuridine, cytarabine, 6-mercaptopurine, 6-thioguanine, fludarabine phosphate, pentostatine, and gemcitabine; natural products and their derivatives (for example, vinca alkaloids, antitumor antibiotics, enzymes, lymphokines and epipodophyllotoxins): vinblastine, vincristine, vindesine, bleomycin, dactinomycin, daunorubicin, doxorubicin, epirubicin, idarubicin, ara-c, paclitaxel (paclitaxel is commercially available as Taxol®), mithramycin, deoxyco-formycin, mitomycin-c, 1-asparaginase, interferons (preferably IFN-α), etoposide, and teniposide.

Other proliferative cytotoxic agents are navelbene, CPT-11, anastrazole, letrazole, capecitabine, reloxafine, cyclophosphamide, ifosfamide, and droloxafine.

Microtubule affecting agents interfere with cellular mitosis and are well known in the art for their cytotoxic activity. Microtubule affecting agents useful in the invention include, but are not limited to, allocolchicine (NSC 406042), halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, epothilone B, and discodermolide (see Service, (1996) Science, 274:2009) estramustine, nocodazole, MAP4, and the like. Examples of such agents are also described in Bulinski (1997) J. Cell Sci. 110:3055 3064; Panda (1997) Proc. Natl. Acad. Sci. USA 94:10560-10564; Muhlradt (1997) Cancer Res. 57:3344-3346; Nicolaou (1997) Nature 387:268-272; Vasquez (1997) Mol. Biol. Cell. 8:973-985; and Panda (1996) J. Biol. Chem 271:29807-29812.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Cytostatic agents that may be used include, but are not limited to, hormones and steroids (including synthetic analogs): 17-alpha-ethinylestradiol, diethylstilbestrol, testosterone, prednisone, fluoxymesterone, dromostanolone propionate, testolactone, megestrolacetate, methylprednisolone, methyl-testosterone, prednisolone, triamcinolone, hlorotrianisene, hydroxyprogesterone, aminoglutethimide, estramustine, medroxyprogesteroneacetate, leuprolide, flutamide, toremifene, zoladex.

Other cytostatic agents are antiangiogenics such as matrix metalloproteinase inhibitors, and other VEGF inhibitors, such as anti-VEGF antibodies and small molecules such as ZD6474 and SU6668 are also included. Anti-Her2 antibodies from Genetech may also be utilized. A suitable EGFR inhibitor is EKB-569 (an irreversible inhibitor). Also included are Imclone antibody C225 immunospecific for the EGFR, and src inhibitors.

Also suitable for use as an cytostatic agent is Casodex® (bicalutamide, Astra Zeneca) which renders androgen-dependent carcinomas non-proliferative. Yet another example of a cytostatic agent is the antiestrogen Tamoxifen® which inhibits the proliferation or growth of estrogen dependent breast cancer. Inhibitors of the transduction of cellular proliferative signals are cytostatic agents. Representative examples include epidermal growth factor inhibitors, Her-2 inhibitors, MEK-1 kinase inhibitors, MAPK kinase inhibitors, PI3 kinase inhibitors, Src kinase inhibitors, and PDGF inhibitors.

Also contemplated herein are conjugates with radiotherapeutic compounds including Radium223.

DETAILED DESCRIPTION

It has been demonstrated in vitro that two drugs may demonstrate synergy at one molar ratio while at other ratios they are additive or even antagonistic (Mayer, L. D., et al., Mol. Cancer Ther. (2006) 5:1854-63; Chou, T-C., et al., Adv. Enzyme Reg. (1984) 22:27-55). Translating such optimal conditions determined in cell culture to animals is challenging due to the increased complexity of animal/mammal system. For example, pharmacokinetic and pharmacodynamic activities of drugs may be significantly different when used alone or present in combination. This provides a challenge when trying to maintain a synergistic molar ratio of two drugs in a target tissue and maintain that ratio for the requisite amount of time to achieve therapeutic benefit. In the cases where drugs have rapid clearance—common for drugs used to treat cancer—it is difficult to achieve a non-antagonistic molar ratio of two drugs in a solid tumor, and even more difficult to maintain a fixed molar ratio for a time sufficient to drive therapeutic benefit, therefore, it is common practice to administer one (or more) of the drugs as a long infusion (e.g. 24 hours) to maintain steady-state exposure to the tumor and then administer a second drug to achieve an effective molar ratio of the two drugs within the tumor. The consequent toxicity of this approach must be managed, this concern highlights another benefit of the current invention—namely reducing systemic exposure by concentrating the drug on the bone and localizing the drug combination to the bone compartment and local area.

Cancer induced bone diseases are intended uses of the current invention, as such primary bone cancer, Osteosarcoma (OS), is provided as a critically relevant example. OS is the most common primary malignant bone tumor and is a disease primarily of adolescents and young adults, often occurring at the metaphyses of long bones. It is a very rare disease with an incidence of only a few hundred cases per year in the United States, and an estimated 20,000 new cases worldwide per year. Multi-agent neoadjuvant chemotherapy is used in OS to achieve a high percent tumor necrosis (% TN) prior to surgery. A strong histologic response (>90% TN) is associated with a longer survival time. High % TN in situ is theorized to be associated with increased survival because a high % TN is likely an indirect measure of response of micrometastases to standard anticancer regimens. In addition to this, in situ tumor necrosis has also been theorized to have an immunomodulating effect favoring host cellular immune response to the tumor. In children, this treatment produces an overall survival rate of ~80%, but event-free survival is lower. In fact, 20% of children diagnosed with OS will not survive 5 years, and up to 50% will not survive 10 years. Most will have significant morbidity associated with the disease. Osteosarcoma is a highly metastatic disease and it is estimated that up to 80% of patients have clinical or subclinical micrometastases at time of initial diagnosis. Patients who present with metastases have a poor prognosis, with long-term survival rates of less than 25%. Clearly, there is need for novel therapies that will improve the outcomes of patients with this disease, as well as other cancer induced bone diseases and bone maladies. Provided herein are novel approaches to achieving molar ratios of drugs and maintaining those ratios in and around the bone for extended periods of times that are not otherwise possible as a means to address a number of these problems.

The ability to target drugs to the bone provides the means of creating drug gradients from the bone towards the circulation (as shown in FIG. 1). Bone targeting drugs can be any biologically active compound with an affinity for any component within or around the bone compartment, this includes but is not limited to the bone mineral, elements of the bone matrix such as collagen, chondroitin sulfate and the cells that make up the bone marrow and surround the bone. Examples of bone targeting agents include but are not limited to, bisphosphonates, bisphosphonate-drug conjugates (such as MBC-11, gemcitabine-ibandronate conjugate—see FIG. 2), antibodies and antibody-drug conjugates targeting bone-related cells (such as Denosumab and Osteoprotegerin (OPG) antibodies), polymeric-amino-acids drug conjugates (asparagine and glutamic acid containing), and tetracycline derivatives. Bone targeting drug conjugates have the ability to release a drug payload from the surface or bone-localized target with known or measurable release rates and can provide special and temporal gradients of drug within the bone compartment. When a second drug is administered in the presence of an established bone localized drug gradient a unique fixed, non-antagonistic drug ratio within the bone compartment is possible.

Thus a bone-targeted drug that can create a drug gradient within the bone compartment, and a second drug that can generate a gradient from the circulation towards the bone surface are the critical components of the method to generate a fixed, non-antagonistic molar ratios of drugs in and around the bone environment for desired periods of time. This method requires administering a pharmaceutical composition comprising a bone-targeted therapeutic agent able to release a drug payload from the bone surface, in addition to a second therapeutic agent administered by any other means, such as intravenously, orally, intraperitoneal or other route of administration.

A surprising aspect of the present methods permits transferring the benefit of a clinically used combination therapy with clinically known ratios of drugs for treatment of soft tissue disease to treatment of bone related disease in the bone compartment.

For example, a combination of gemcitabine and docetaxel combination can now be used in the treatment of osteosarcoma, comprising administering a pharmaceutically effective amount of a conjugate of gemcitabine-ibandronate in combination with a pharmaceutically effective amount of docetaxel to a patient in need thereof.

The method of creating fixed, non-antagonistic molar ratios of drugs in and around the bone environment for desired periods of time as described above can be applied to:
 bone-related disease when the malady is cancer-induced bone disease or primary bone cancer,
 bone-related disease such as osteomyelitis;
 bone-related disease such as viral replication within the bone marrow;
 bone pain;
 rheumatoid arthritis or inflammation in or around the bone; or
 metabolic disease affecting the bone.

The method can be applied where the treatment of the bone environment by a combination of drugs not previously used clinically is desirable due to compelling data in cell based studies or animal based studies, or due to the mechanism of the drugs in combination having compelling additive or synergistic effects (e.g. radiosensitization).

The kinetics of drug release from the bone will direct some bone targeting agents to be used by the method where the second therapeutic agent is administered prior to administration of the bone-targeted therapeutic agent, for example, up to 48 hours prior to the administration of the bone-targeted therapeutic agent. In this manner the desired molarity of the non-bone-targeted drug can be established in the bone compartment, or in order to provide for clearance on a certain time scale, such that the subsequent bone targeted drug and consequential release from bone optimizes the therapeutic benefit.

In other aspects, the second therapeutic agent can be administered after the bone-targeted therapeutic agent, for example, up to 48 hours after the bone-targeted therapeutic agent.

And in yet other embodiments or with other combinations of drugs, the second therapeutic agent will be administered during the administration of the bone-targeted therapeutic agent.

The benefits of MBC-11 as a single agent in treating cancer induced bone disease has been established in animal models and clinically. Further clinical benefit is achieved where the bone-targeted therapeutic agent is MBC-11 and the second therapeutic agent is docetaxel.

In addition, the potential of MBC-11 to release cytarabine to the bone such that it radiosensitizes radiotherapeutic drugs will benefit patients where the bone-targeted therapeutic agent is MBC-11 and the second therapeutic agent is Xofigo.

The current clinically established MTD of MBC-11 indicates the method should be used where MBC-11 is administered at or below 5/mg/kg/day via a 2-hour infusion for up to 5 consecutive days and Xofigo is administered at or below the standard of care dosing regimen.

Gemcitibine is known to be a potent sensitizer of docetaxel, often more potent than cytarabine and able to self-potentiate its own activity in addition to sensitizing. Therefore, it is contemplated herein that the method is useful where the bone-targeted therapeutic agent is a conjugate of Gemcitabine-to-Ibandronate and the second therapeutic agent is docetaxel.

Gemcitibine is known to be a potent radiosensitizer, often more potent than cytarabine and able to self-potentiate its own activity in addition to radiosensitizing. Therefore the method where the bone-targeted therapeutic agent is a conjugate of Gemcitabine-to-Ibandronate and the second therapeutic agent is Xofigo is clinically beneficial.

The MTD of the conjugate of Gemcitabine-to-Ibandronate is lower than that of MBC-1. Therefore, a conjugate of Gemcitabine-to-Ibandronate can be administered at or below 5/mg/kg/day via a 2-hour infusion for up to 5 consecutive days and Xofigo administered at or below its standard of care dosing regimen.

The following experimental results and prophetic examples are provided for purposes of illustration and are not intended to limit the scope of the invention.

EXAMPLES

The following examples are provided for illustrative purposes only and are not intended to limit the scope of the invention.

Example 1

The goal of following studies was to evaluate the efficacy of the Gemcitabine-Ibandronate (GEM-IB) conjugate. GEM-IB was tested both alone and in combination with docetaxel (DTX) and compared to equimolar amounts of the individual free compounds (GEM, DTX, and IB). Objectives were to first test a range of doses of GEM and DTX to determine optimal conditions for testing with a mouse osteosarcoma (OS) model. Tumor burden and bone morphology in mice treated with either conjugate or free compounds was subsequently analyzed.

Dosing range for GEM and GEM/DTX combination: GEM and DTX in combination were found to have synergistic activity. This was determined in culture with a human OS cell line—143B-luc (143B cells were transfected to express luciferase (luc) for use in a mouse model system). Upon treatment of these cells in culture, the combination of drugs exhibited lower IC50 values than the individual drug agents; DTX IC50=72 nM, GEM IC50=9 nM; in the presence of 1 nM GEM the IC50 of DTX was reduced 600-fold to 0.12 nM. Bliss analysis suggested that the two drugs were synergistic at DTX doses ranging from 10 pM-1 mM with GEM at 0.5 or 1 nM. This provided a large range of drug ratios to target to the bone microenvironment.

143B-luc cells were then implanted into nude mice via intratibial injection, creating an orthotopic model for OS. The presence and growth of tumors was confirmed with in vivo imaging (Xenogen). Mice (N=8/treatment group) were then treated with 60 mg/kg GEM twice weekly and 15 mg/kg DTX once weekly, alone or in combination (15 mg/kg DTX with 20, 40 or 60 mg/kg GEM) and monitored for weight loss and tumor growth. Mice in all treatment groups, except for the highest combination dose, did not exhibit any weight loss, indicating tolerance of the treatment and drug combination. Tumor size was monitored by measuring the largest diameter of the tumor-bearing leg (luminescence did not correlate with tumor size in this model and was used only for normalizing the animal groups when tumor take was initiated). The three combination groups showed even lower tumor growth, with the highest combination treatment showing the lowest tumor growth. Notably, the 60 mg/kg GEM alone group showed similar tumor growth to the 20 mg/kg GEM with 15 mg/kg DTX group, suggesting the addition of DTX allowed a much lower dose of GEM to show a similar reduction in tumor size.

Efficacy of GEM-IB (shown in FIG. 2): GEM-IB, a second-generation conjugate, is hypothesized to target GEM to bone and thus increase its efficacy against OS alone and in combination with DTX. Additionally, bisphosphonates themselves are demonstrated to have anti-tumor effects, further contributing another mechanism of action to those of GEM and DTX. GEM-IB was then used in a OS mouse model alone and in combination with DTX.

Tolerability for IB and GEM-IB was tested in a mouse model system. IB treatment of 12 mg/kg twice weekly caused only minimal weight loss and GEM-IB treatment of 14 mg/kg twice weekly showed similar results. To ensure the health of mice throughout a longer study, doses were reduced to 6 mg/kg IB and equimolar doses of GEM-IB (14 mg/kg) and GEM (6 mg/kg) with 15 mg/kg DTX. Mice were implanted with the 143B-luc cells via intratibial injection and treatment started 4 days after implantation. In vivo MicroCT was performed 22 days after starting treatment, confirming bone preservation effects of GEM-IB and/or IB with the observation of high bone volume density and trabecular number in mice receiving IB alone or GEM-IB.

Figure 1A:
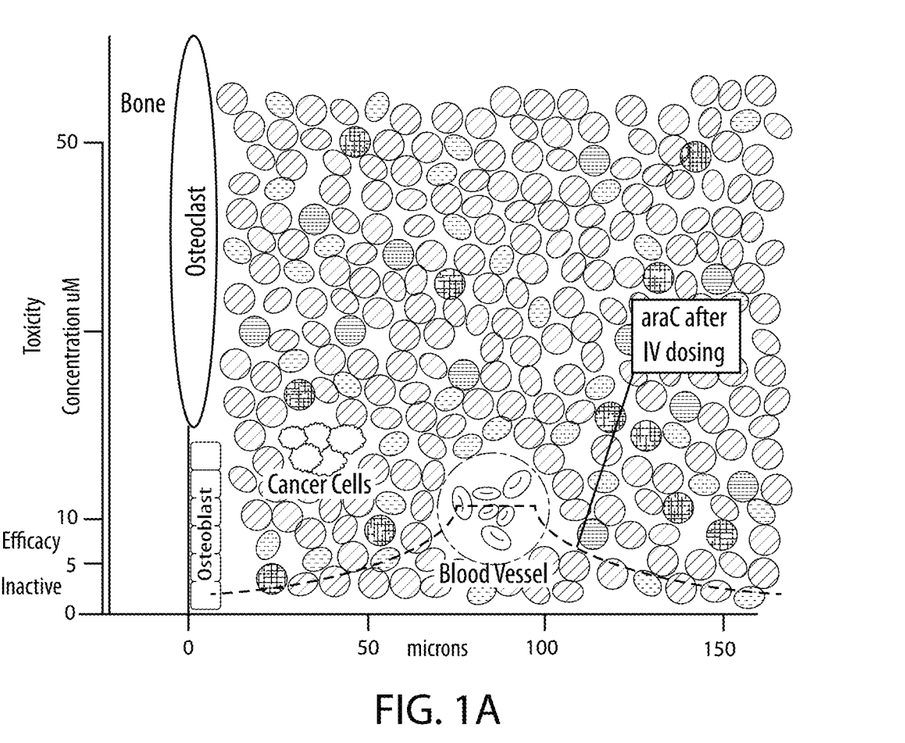
Figure 1B:
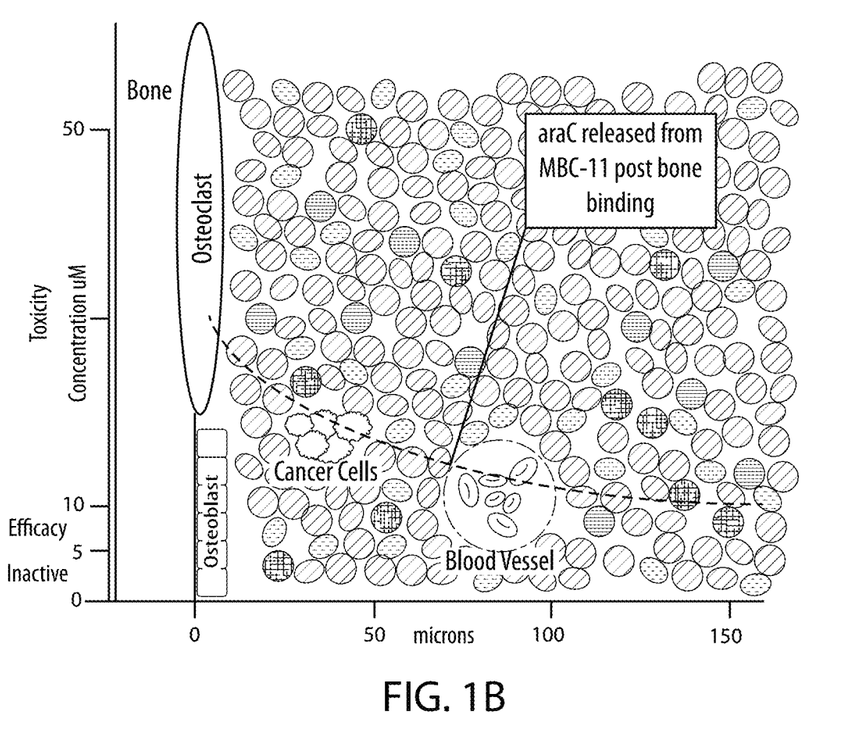
Figure 1C:
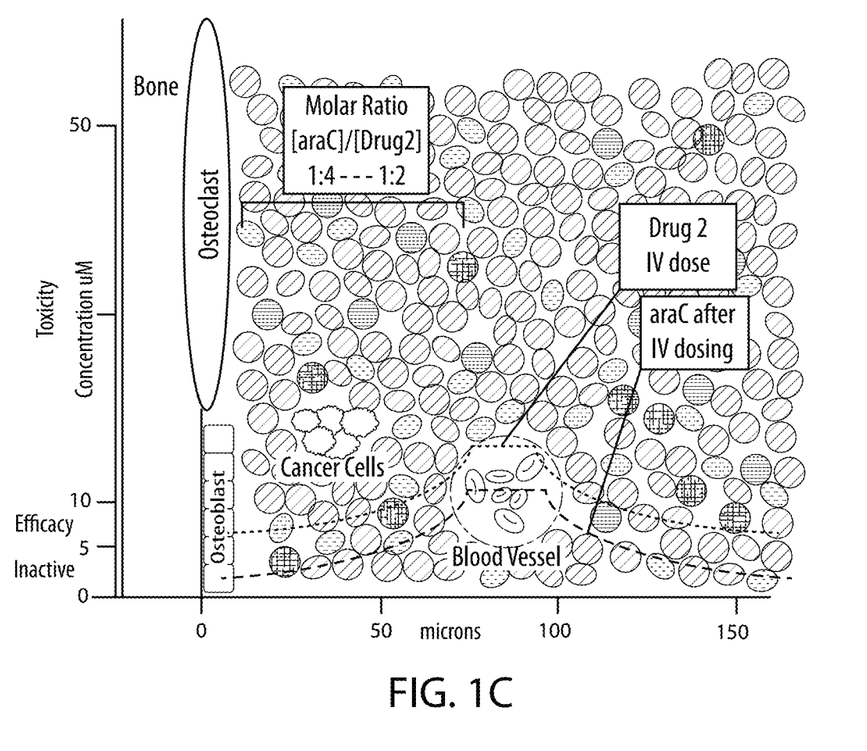
Figure 1D:
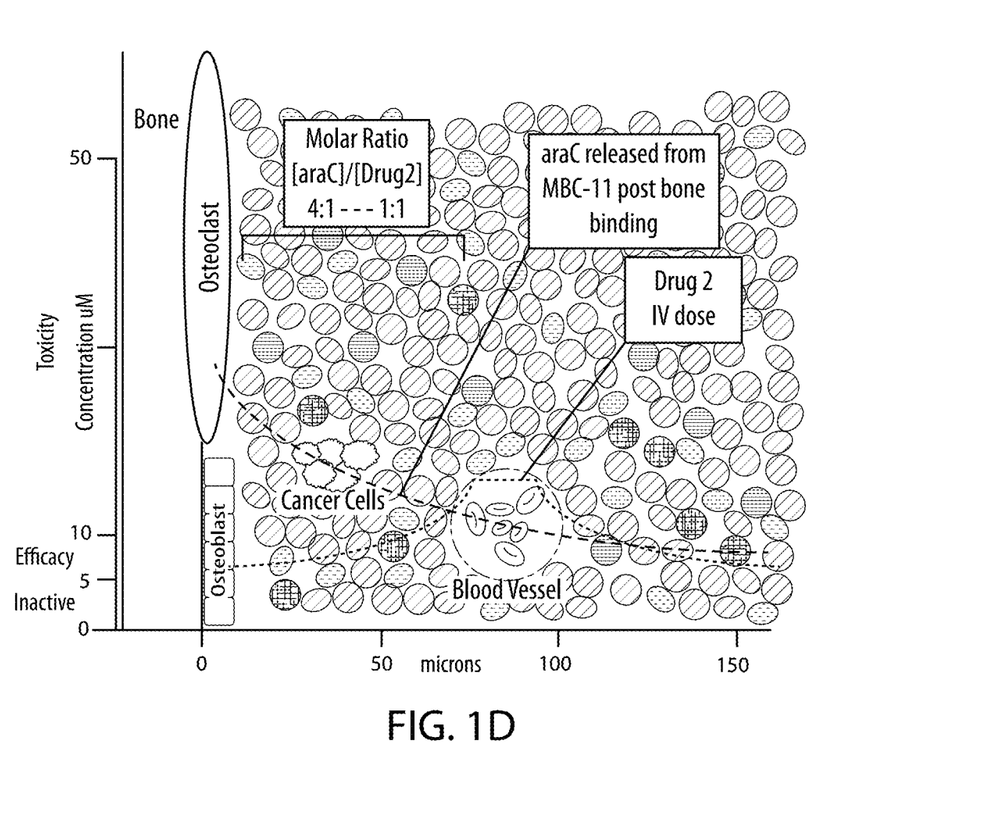
Figure 2:
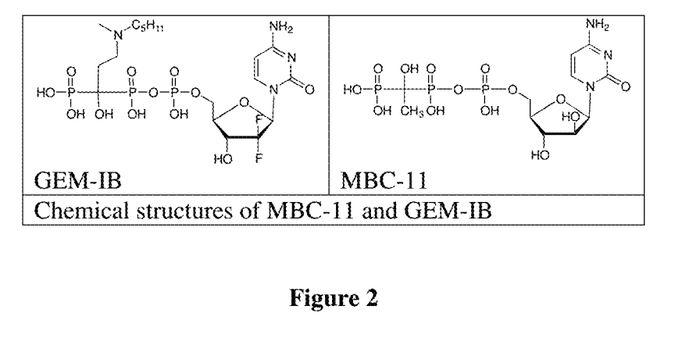
Figure 3:
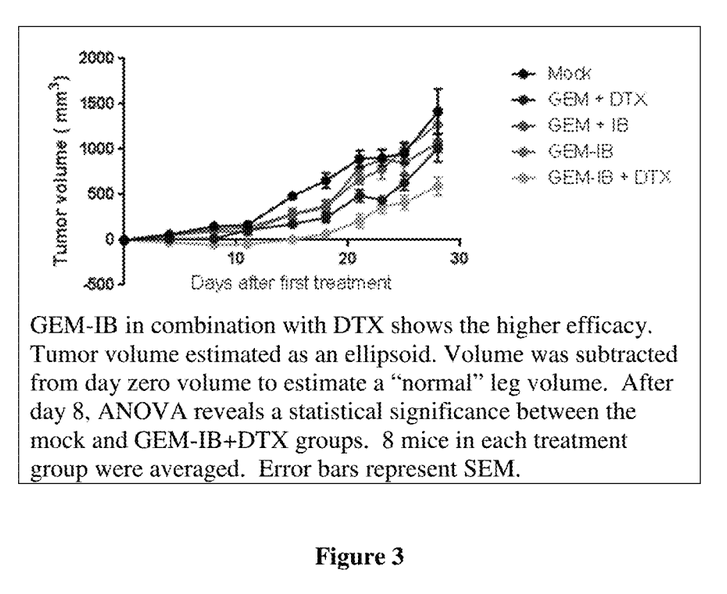
FIG. 3 illustrates the benefit of GEM-IB in combination with docetaxel with regard to tumor reduction and survival benefit in a murine model of osteosarcoma. GEM-IB in combination with DTX shows the higher efficacy. Tumor volume estimated as an ellipsoid. Volume was subtracted from day zero volume to estimate a "normal" leg volume. After day 8, ANOVA reveals a statistical significance between the mock and GEM-IB+DTX groups. 8 mice in each treatment group were averaged. Error bars represent SEM.

Unconjugated GEM in combination with DTX or IB showed only a slight reduction in tumor growth; presumably due to the 10-fold reduction in GEM as compared to the most efficacious combination noted above. The conjugate GEM-IB at 14 mg/kg showed a similar slight reduction compared to free agents. The greatest reduction in tumor growth was shown by GEM-IB in combination with DTX (FIG. 3). Thus, the conjugate of ibandronate (IB) and GEM (Gemcitabine-to-Ibandronate GEM-IB of FIG. 2) is efficacious as a single agent and demonstrated additive benefit in combination with DTX in a murine OS model system. Equivalent efficacy is demonstrated with constant DTX while GEM-IB was administered at $\frac{1}{10}$ the molar dose of free GEM. This innovative therapy can be provided to OS patients in compositions, combinations, and methods provided herein.

This is evidenced by both measurement of the largest tumor diameter only (data not shown), and tumor volume estimation (FIG. 3). Notably, the bone targeted combination rivaled the efficacy seen with the free agents despite the molar equivalent of the GEM moiety being reduced 10-fold with the conjugate.

Figure 4:
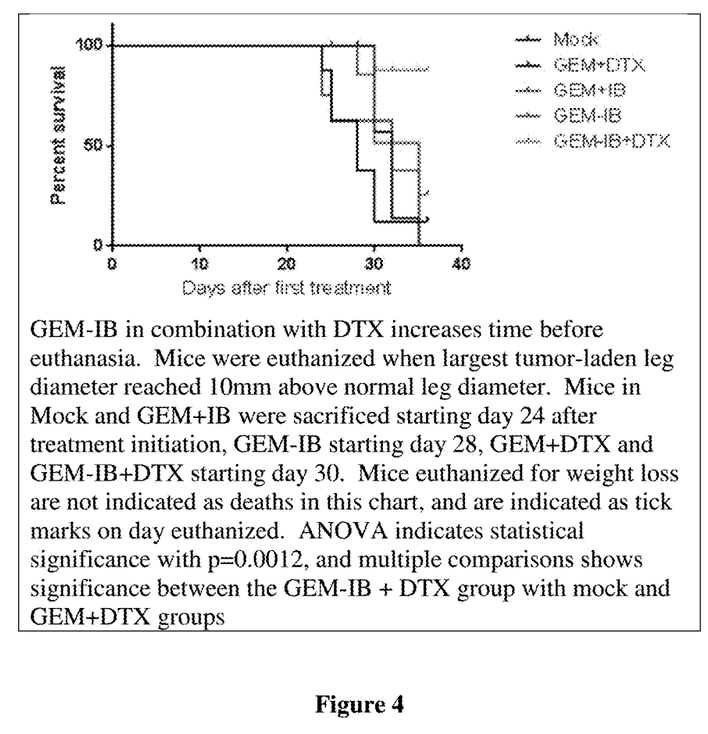

Kaplan-Meier analysis of survival of mice until euthanasia due to large tumor size further demonstrates improved survival with the GEM-IB and DTX combination (FIG. 4). The large reduction in tumor growth exhibited by the GEM-IB conjugate in combination with DTX demonstrates increased efficacy by a targeted chemotherapeutic agent, and synergistic action with DTX.

Conclusions

These results showed promising in vivo anti-tumor and bone-preserving effects of the targeted GEM-IB treatment in combination with DTX consistent with the synergy of GEM and DTX observed in vitro. The OS mouse model provides a drug testing system with tumors in the orthotopic location and the ability to confirm tumors with in vivo imaging.

Treatment of mice with IB alone or in the GEM-IB conjugate showed possible nephrotoxicity at higher levels, but was well tolerated at lower doses. Mice were then treated with GEM-IB, GEM-IB with DTX, or the individual agents of GEM, DTX, or IB. Mice treated with GEM-IB+DTX showed the greatest reduction in tumor growth. This was demonstrated by both tumor measurement and by increase in survival time before necessary euthanasia. Efficacy studies in mice demonstrated reduced tumor growth when administered the specific conjugate of gemcitabine to ibandornate as shown in FIG. 2 at a doses ranging >100-fold (0.1-14 mg/kg) when administered with docetaxel at 15 mg/kg. Cell-based studies demonstrated this combination provided osteosarcoma cancer cell killing activities with docetaxel ranging 10,000-fold (0.01-1000 micromolar) when Gemcitibine was present at 0.5-1 nM. Together these studies indicate our ability to generate efficacious ratios of drug in the bone compartment that is greater than the efficacy possible in the absence of bone targeting. Our data suggests dosing of GEM-IB over a 100-fold range provides benefit in the presence of docetaxel. Osteosarcoma cell based data suggests the docetaxel dose range can cover the very wide range of 10,000. Thus, generalizing the cell-based and mouse data to treating a mammal with osteosarcoma calls for dosing GEM-IB between a range of (0.02-14 mg/kg) with docetaxel dosed between 1.5 micrograms/kg-15 milligrams/kg).

Example 2

Figure 5:
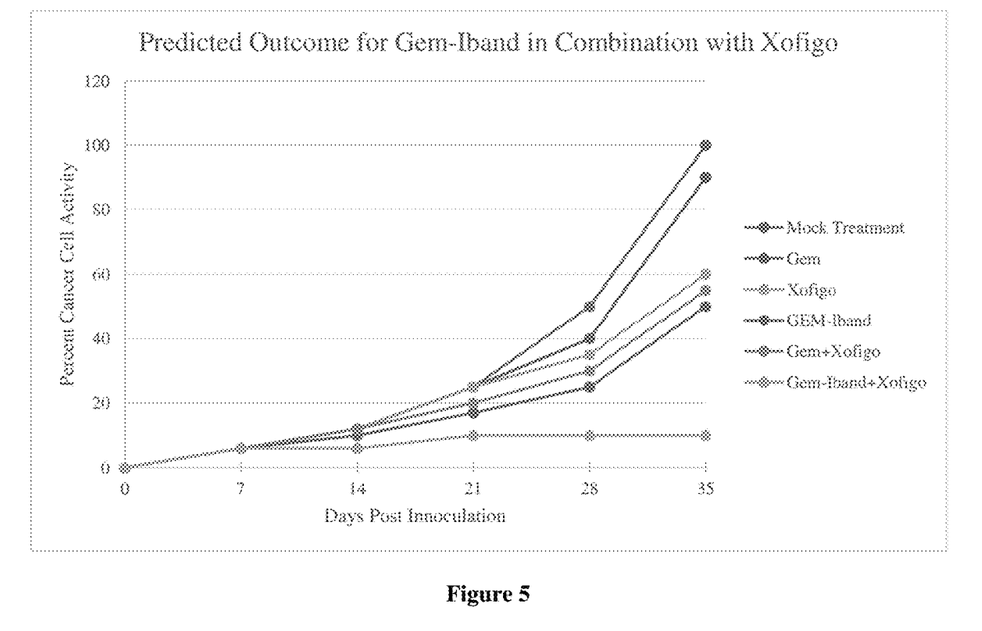

Prophetic example of in vivo demonstration of non-antagonistic efficacy of Xofigo in combination with Gem-Iband (Gemcitabine-Ibandronate conjugate) in a xenograft mouse model of osteosarcoma (OS). This example is predicated on the reports of gemcitabine's ability to radiosensitize cells. See FIG. 5.

Mice injected orthotopically with KRIB cells will develop radiographic evidence of lytic/blastic OS lesions and gross pulmonary metastases within 4 weeks after orthotopic injection (Berlin, O., et al., Cancer Research (1993) 53, 4890-4895). KRIB cells have been stably transfected allowing constitutive expression of luciferase; 2×104 cells in 10 uL per will be injected into the medullary cavity of the tibia in 6-8 week old male athymic mice. The following treatments will be initiated 7 days post-inoculation and continued for 5 weeks:

20 mg/kg Gemcitabine twice per week.
SOC Xofigo once per month.
Gem-Iband at a molar equivalent of 20 mg/kg Gemcitabine twice per week.
20 mg/kg Gemcitabine twice per week in addition to Xofigo once per month.
Gem-Iband at a molar equivalent of 20 mg/kg Gemcitabine twice per week in addition to Xofigo once per month.
Mock treatment.

What is claimed is:

1. A method of treating a subject having cancer induced bone disease or primary bone cancer, the method comprising administering to the subject (i) a pharmaceutical composition comprising a bone-targeted therapeutic agent:

in combination with (ii) docetaxel; wherein the bone-targeted therapeutic agent is administered at a dose ranging from 0.02 to 14 mg/kg and the docetaxel is administered at a dose ranging from 1.5 micrograms/kg to 15 milligram/kg.

2. The method of claim 1, wherein the primary bone cancer is osteosarcoma.

3. The method of claim 1, wherein the subject has cancer induced bone disease.

4. The method of claim 1, wherein a molar ratio of the bone-targeted therapeutic agent with the docetaxel is derived from cell based or animal based studies.

5. The method of claim 1, wherein the docetaxel is administered up to 48 hours prior to the administration of the bone-targeted therapeutic agent.

6. The method of claim 1, wherein the docetaxel is administered up to 48 hours after the bone-targeted therapeutic agent.

7. The method of claim 1, wherein the docetaxel is administered during the administration of the bone-targeted therapeutic agent.

8. The method of claim 1, wherein the docetaxel is administered at an amount from $\frac{1}{100}$th up to its standard dosing while administration of the bone-targeted therapeutic agent is at its standard dosing.

9. The method of claim 1, wherein the docetaxel is administered at its standard dosing while administration of the bone-targeted therapeutic agent is in an amount from $\frac{1}{100}$th up to standard dosing.

10. The method of claim 1, wherein the docetaxel is administered at an amount from $\frac{1}{100}$th up to its standard dosing while the bone-targeted therapeutic agent is administered at an amount from $\frac{1}{100}$th up to its standard dosing.

11. The method of claim 1, wherein the bone-targeted therapeutic agent is administered at or below 5 mg/kg/day via a 2-hour infusion for up to 5 consecutive days.

12. The method of claim 1, wherein the subject has a primary bone cancer.

* * * * *